United States Patent [19]

Shoney

[11] 4,210,478
[45] * Jul. 1, 1980

[54] METHOD OF MAKING A CATHETER

[75] Inventor: Suryakant R. Shoney, Cranston, R.I.

[73] Assignee: International Paper Company, New York, N.Y.

[*] Notice: The portion of the term of this patent subsequent to Feb. 11, 1992, has been disclaimed.

[21] Appl. No.: 856,861

[22] Filed: Dec. 2, 1977

Related U.S. Application Data

[60] Continuation of Ser. No. 655,636, Feb. 5, 1976, abandoned, which is a continuation-in-part of Ser. No. 539,298, Jan. 8, 1975, abandoned, which is a division of Ser. No. 358,309, May 8, 1973, Pat. No. 3,865,666.

[51] Int. Cl.² .............................................. B29C 11/00
[52] U.S. Cl. ............................... 156/242; 128/349 B; 156/244.13; 156/245; 156/294; 264/248; 264/250; 264/259; 264/271; 264/275; 264/294

[58] Field of Search .............. 128/348, 349 R, 349 B, 128/349 BU, 350 R, 350 U, 351; 156/242, 245, 293, 294; 264/248, 250, 259, 271, 275, 279, 294, 328

[56] References Cited

U.S. PATENT DOCUMENTS

| Re. 27,910 | 2/1974 | Birtwell | 128/349 B |
|---|---|---|---|
| 3,112,748 | 12/1963 | Colburn | 128/350 R |
| 3,288,901 | 11/1966 | Clark | 264/267 |
| 3,528,869 | 9/1970 | Dereniuk | 156/294 |
| 3,734,100 | 5/1973 | Walker et al. | 128/351 |
| 3,812,860 | 5/1974 | Gilbert et al. | 128/349 B |
| 3,832,253 | 8/1974 | Palma et al. | 128/349 BU |
| 3,865,666 | 2/1975 | Shoney | 128/349 B |
| 3,884,242 | 5/1975 | Bazell et al. | 128/351 |
| 3,959,429 | 5/1976 | Benning | 264/250 |

*Primary Examiner*—Caleb Weston
*Attorney, Agent, or Firm*—Richard M. Barnes

[57] ABSTRACT

Disclosed is a catheter and a method of manufacturing such a catheter. The method includes either the steps of molding the catheter tip onto the shaft, or molding a balloon onto the shaft, or both.

19 Claims, 11 Drawing Figures

METHOD OF MAKING A CATHETER

This is a continuation of application Ser. No. 655,636, filed Feb. 5, 1976, now abandoned which in turn was a continuation-in-part of application Ser. No. 539,298, filed Jan. 8, 1975, now abandoned, which in turn was a division of application Ser. No. 358,309, filed May 8, 1973, now U.S. Pat. No. 3,865,666.

BACKGROUND OF THE INVENTION

1. Field to Which the Invention Pertains

Well known to physicians is the fact that individuals may, for a variety of reasons, lose control of their urinary function. Although the reasons for the loss of urinary control are manifold, the consequent treatment is a rather well accepted medical practice which involves inserting a tube or catheter up the urinary passage until the remote or distal end is located within the bladder. The near or proximal end of the catheter remains outside of the body and there is thus provided a path or means through which the bladder may drain. Once a catheter has been passed through the urinary tract and inserted into the bladder, it is generally medically desirable to have the catheter retained in the urinary tract with the distal end of the catheter positioned within the bladder. Catheters which are designed for such a function are called urinary retention catheters and are generally provided with some means to promote retention. Typically, this retention capability is provided by including an inflatable balloon at the distal end of the catheter. During insertion, the balloon is deflated. After the distal end of the catheter is positioned within the bladder, the balloon is inflated by passing a fluid, typically water, through a passage within the catheter which is referred to as an inflation lumen. When the balloon is inflated, the inflation lumen is sealed and the inflated balloon within the bladder insures retention. Thereafter, the bladder may drain through a second passage within the catheter, i.e. the drainage lumen.

There are a number of medical procedures which involve the use of catheters and, as a result, catheters are generally referred to by a name associated with their function, e.g. urinary catheters, tracheal catheters, venous catheters, etc. While all such catheters must be fabricated so as to insure the safety and comfort of the patient, the physiological demands imposed upon a urinary retention catheter are particularly severe and appear to result in conflicting design criteria. For example, the comfort of the patient dictates that a urinary retention catheter be as soft and as flexible as possible. On the other hand, from a structural point of view, such a catheter must be sufficiently rigid to insure that as it traverses the urinary tract, the catheter tube will not bend to an extent which results in occluding or reducing the size of the drainage lumen and the inflation lumen. Similarly, it is clearly desirable that the outer diameter of the catheter be as small as possible while the diameter of the drainage lumen be as large as possible. However, the maximum outer diameter of the catheter is substantially defined by the diameter of the urinary tract and the comfort of the patient while the contractive forces which are exerted on the catheter by the urinary tract substantially define a minimum wall thickness between the drainage lumen and the exterior of the catheter.

Of substantial concern to both the patient and the physician is the balloon and its proper inflation. After the catheter is inserted, it is desirable that the balloon be so constructed and arranged that it can be inflated with a minimum inflation pressure. Such an objective is desirable because the maximum inflation pressure required to inflate a balloon will be the determining factor with respect to the minimum wall thickness surrounding the inflation lumen. Since one desires to maximize the size of the drainage lumen and since the area occupied by the inflation lumen diminishes the size of the drainage lumen, it follows that one wishes to utilize a minimum wall thickness for the inflation lumen and, therefore, the balloon construction should be such as to require a minimum pressure for inflation. While one may construct a urinary retention catheter having a balloon which will inflate with a minimum pressure, the resulting structure may, and often does, possess undesirable features. For example, to achieve a low inflation pressure, a soft and pliant material may be used for the balloon. However, from a manufacturing point of view, it is generally most economical to fabricate the balloon as an integral part of the catheter tip and, thus, the catheter tip will also be soft and pliant. Constructions of this type, which are known to the prior art, unfortunately possess certain disadvantages which are discussed hereinafter.

Finally, urinary retention catheters must not only meet or exceed the various medical and patient oriented criteria discussed above but, in addition, such a catheter must be of a construction which lends itself to a method of high volume, low cost manufacture. Such manufacturing criteria are particularly significant with respect to urinary retention catheters since tolerances are critical yet the cost of the resulting product must be consonant with the disposable nature of the product.

The invention disclosed herein relates to novel catheters and the method of manufacturing such catheters.

2. Prior Art

In an attempt to satisfy the various and conflicting criteria heretofore discussed, the prior art reflects an evolution of catheter designs. For several decades, all urinary retention catheters were manufactured by a dipping process wherein two longitudinally adjacent wires were dipped in a latex bath until a catheter tube of the desired diameter was built up. Subsequently, a hole was pierced through the wall of the tube at one end and communicated with the cavity formed by one of the two wires, which cavity would later be the inflation lumen. Thereafter, a release agent was deposited around the tube in the area of the hole and the end of the tube was again dipped to build up another layer of latex at the end of the tube and which would constitute the balloon.

The catheter which resulted from this method of manufacture was widely accepted. However, certain disadvantages of the catheter construction by this method of manufacture have been recognized. One disadvantage arises from the dipping process whereby precise dimensional control of the catheter diameter tends to be problemsome which, in turn, tends to increase the manufacturing cost.

While the strength and elasticity of latex rubber renders that material ideal as a catheter material, it has been found that, as do most materials, it poses a degree of susceptibility to encrustation from the salts commonly found in urine. On the other hand, recent developments in materials technology have made available the silicone rubbers which promise to be relatively free of susceptibility to encrustation.

Thus, more recent prior art catheter constructions have embodied silicone rubber tubes for the tip and body to relieve the encrustation problem and to enjoy a further advantage of compatibility with human tissues. Although the prior art has established that silicone rubber is an acceptable material for a catheter, the problem still remains as to the structure of the catheter and the method of manufacturing a particular structure. The problems associated with prior art silicone rubber catheter constructions is exemplified by the catheter construction disclosed by Birtwell in U.S. Pat. No. 3,547,126. The Birtwell construction employs an extruded silicone tube as the body of the catheter in combination with a molded silicone tip which is provided with a rearwardly extending portion. The rearwardly extending portion is attached to the catheter tube or body and forms the inflation balloon. The tip portion, which is abuttingly affixed to the tube or body portion, is provided with a drainage lumen that must be aligned with the drainage lumen in the body of the catheter. Because of this construction, a number of problems arise both in the manufacture of the catheter and in the use thereof. For example, as previously stated, it is desired that the pressure required to inflate a balloon should be as low as possible and thus the balloon material should be soft and relatively elastic. However, in a catheter construction of the type disclosed by Birtwell, the tip and balloon are molded as one piece and, therefore, the tip will have the same mechanical properties as the balloon. Since the tip extends longitudinally substantially beyond the end of the extruded tube and since the material used to form the tip will have a low modulus of elasticity in order to insure that the balloon is easily inflated, the tip may deflect and bend during insertion, i.e. the tip portion does not possess the required rigidity. Moreover, in the Birtwell construction any bending of the tip is especially deleterious because of the glued, butt joint connection between the tip and the body, i.e. any bending of the tip will tensionally stress the bond between the tip and the body with the probable result of a failure of the bond.

Finally, because the tip in the Birtwell construction includes a drainage lumen, assembly of the tip and the tube is exacting if a misalignment is to be avoided. The problem of avoiding a misalignment during the assembly of the tip and the tube is economically significant since the avoidance of such misalignment requires that one must resort to either a manual assembly or a sophisticated mechanical assembly.

Another manufacturing difficulty associated with catheters of the type disclosed by Birtwell relates to the problems of the bond between the tip and the tube. More particularly, since this bond is essentially a butt joint, an adhesive of extraordinary strength is required. Indeed, in practice, it has been found to be difficult to locate an adhesive which is sufficiently strong to withstand the stresses to which this joint is subjected. In addition, however, even if an adhesive of sufficient strength is employed, it has been found that when the adhesive sets the tip is often longitudinally misaligned with the tube. While the cause of the misalignment phenomenon is not clearly understood, it is believed that the problem may arise from either an uneven amount of adhesive being initially deposited on the tip or, alternatively, from an uneven drying or curing of the adhesive. In any event, the problem is manifest and is present almost to the point of precluding economic manufacture of such a construction.

The catheter construction disclosed hereinafter and the method of manufacture substantially overcomes all of the problems associated with prior art catheters and their method of manufacture.

SUMMARY OF THE INVENTION

A catheter is provided in which either (1) the tip is insert molded onto the shaft, i.e. a tip is molded and simultaneously bonded to the shaft, or (2) the balloon is insert molded onto the shaft, i.e. a balloon is molded and simultaneously bonded onto the shaft, or (3) both the tip and balloon are insert molded onto the shaft.

To insert mold the balloon onto a shaft, an elastomeric shaft, preferably a partially cured, extruded rubber silicone shaft, is inserted into a mold. The shaft includes a drainage lumen extending longitudinally for the entire length thereof and an inflation lumen which extends longitudinally of the shaft for at least a major portion thereof and communicates with the exterior of the shaft through an aperture located adjacent to the distal end of the shaft. Within the mold, a balloon is insert molded onto the shaft. Thereafter, the shaft and balloon are removed from the mold and the distal end of the balloon is bonded to a catheter tip which was attached to the catheter shaft either before or after the balloon was insert molded onto the shaft.

To insert mold a tip onto a shaft, an elastomeric shaft is inserted into a mold. The shaft contains at least a drainage lumen extending the entire length thereof. Within the mold, a tip is insert molded onto the shaft. At least one drainage eye is provided through the tip and communicates with the cavity therein.

DESCRIPTION OF THE PREFERRED EMBODIMENTS

Figure 1:
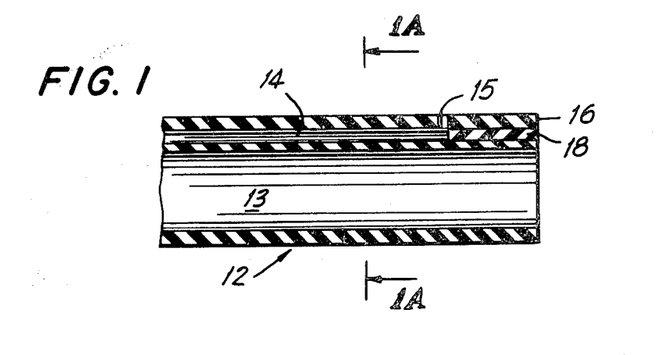
FIGS. 1–4 illustrate the product resulting from the method steps which comprise one embodiment of my invention.

Referring to FIG. 1, there is shown, in section, the distal end of a catheter shaft for use in one embodiment of my invention. Only the distal end of the catheter shaft is shown since the remainder of the shaft is the same as that section of the shaft which is on the left side of the section line 1a.

It will be seen that the catheter shaft 12 includes a drainage lumen 13 and an inflation lumen 14. The shaft 12 is made of an elastomeric material and, preferably, is made of extruded silicone rubber. In the event that the shaft 12 is extruded, the drainage lumen 13 and the inflation lumen 14 will extend longitudinally of the shaft for the entire length thereof. Of course, subsequent to the extrusion of the shafts, the substantially continuous extruded shaft is cut to the desired length. If the shaft 12 is provided with an inflation lumen 14 which extends for the entire longitudinal length thereof, the shaft is provided with an aperture 15 adjacent to the distal end 16 of the shaft 12. The aperture 15 provides communication from the inflation lumen 14 to the exterior of the shaft 12. Preferably, the inflation lumen 14 is plugged by a material 18 between the aperture 15 and the distal end 16 of the shaft 12.

Figure 1A:
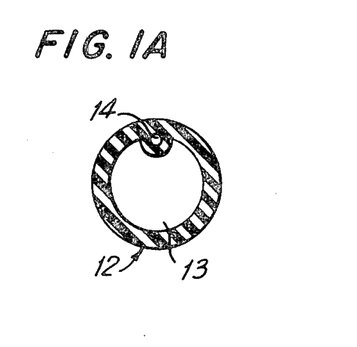
FIG. 1A is a view, in section, taken along the section lines 1a—1a of FIG. 1.

Referring to FIG. 1a, one form of the interior of a shaft of the type shown in FIG. 1 is illustrated.

Figure 5:
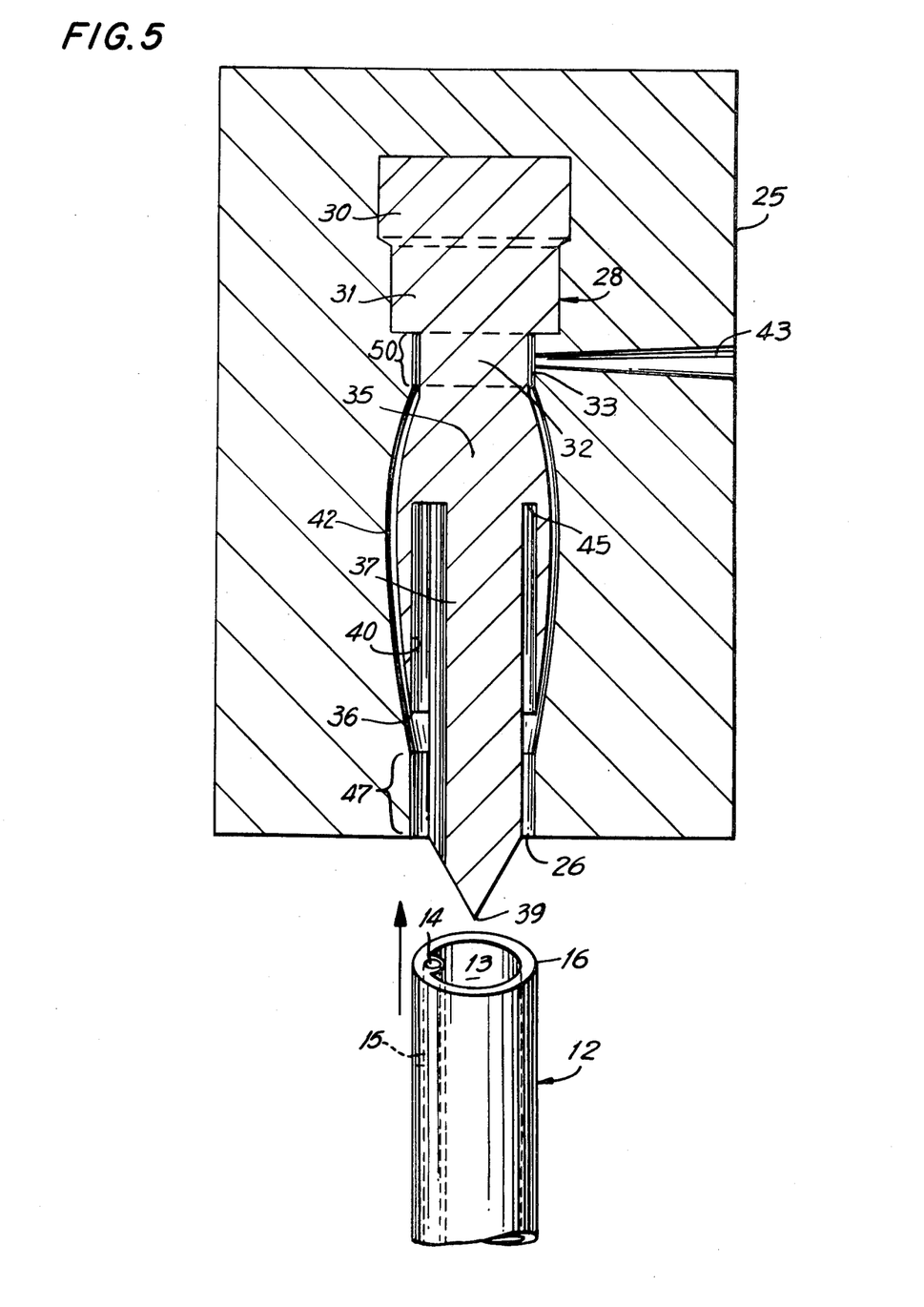
FIG. 5 is a view, in section, of a mold used in the practice of my process.

Referring now to FIG. 5, there is shown an apparatus which may be used in the practice of a step of my process. More specifically, there is shown, in section, a mold 25 having a cavity 26. Fixedly disposed within the cavity 26 is a mandrel, generally indicated as 28. The mold 25 is a two piece mold which may be longitudinally separated to expose the cavity 26. When the mold 25 is thus split apart, the mandrel 28 may be placed within the cavity 26 and maintained in place by the alignment heads 30 and 31, i.e. the alignment heads 30 and 31 are engagingly received in appropriately shaped cavities. Depending downwardly from the alignment head 31 is a cylindrical section 32 which, together with the adjacent interior walls of the mold 25 defines an annulus 33. Depending downwardly from the cylindrical section 32 is a diverging converging section 35 which terminates at 36. The walls of the section 35, together with the correspondingly shaped wall of the interior of the mold 25, define a diverging-converging annulus.

Returning to a description of the mandrel 28, it may be noted that a section 37 thereof depends downwardly past the edge 36 and terminates at a point 39 exteriorly of the mold 25. Additionally, an interior annulus 40 is defined by the downwardly depending section 37 and a portion of the converging wall.

The annulus 33 and the annulus 42 are in fluid communication with the exterior of the mold 25 of the feed channel 43.

In accordance with my process, a mold and mandrel of the type shown in FIG. 5 is assembled and a catheter shaft 12 is inserted into the cavity 26 and over the extension 37 of the mandrel 28. Preferably, the exterior of the extension 37 is appropriately shaped to engagingly correspond to the drainage lumen of the catheter 12. The catheter 12 is inserted into the cavity 26 until the distal end 16 thereof abuts the flat portion 45. When the catheter shaft 12 is thus received in the mold 25, it will be noted that the portion 47 of the wall of the cavity 26 will surroundingly engage the exterior of the catheter 12. Additionally, it may be noted that the longitudinal length of the annulus 40 is sufficient to insure that the aperture 15 will be located therein.

When the catheter shaft 12 is so disposed within the mold 25, an elastomeric material is injected, under pressure, through the feed channel 43 to fill the annulus 33 and the annulus 42. Preferably, the elastomeric material injected through the feed channel 43 is a catalyzed, heat curable silicone rubber. If such a material is used, the entire mold is heated by any convenient means in order to catalyze and initially set the silicone rubber. When the silicone rubber has been partially cured, the mold 25 is opened and the catheter shaft 12 and the mandrel 28 are removed.

Figure 2:
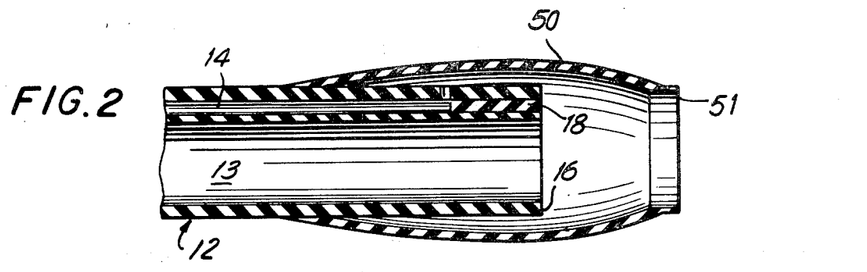

Referring to FIG. 2, there is shown the product which results from the process step heretofore described. More particularly, it will be noted that the catheter shaft 12 has been provided with a balloon 50 which is molded to the catheter shaft 12 adjacent to the distal end 16 thereof but proximally of the aperture 15. In accordance with this embodiment of my invention, the balloon 50 extends past the distal end 16 of the shaft 12. Also, it may be noted from FIG. 2 that the internal diameter of the distal end 51 of the balloon is slightly less than the external diameter of the shaft 12. Similarly, careful inspection of FIG. 2 will reveal that the thickness of the distal end 51 of the balloon 50 is less than the thickness of the remainder of the balloon. While the structural reasons for these particular dimensional relationships will become apparent hereinafter, the method by which these dimensions are obtained will now be described.

Referring again to FIG. 5, it may be noted that the diameter of the section 50 of the cavity 26 is less than the diameter of the cavity 26 in the section 47 but is greater than the diameter of the extension 37. Thus, with this relationship, the portion of the balloon 50 which is formed in the annulus 33 will have an internal diameter which is less than the external diameter of the catheter shaft 12.

Similarly, in FIG. 5 it will be noted that the cavity 26 and the portions 32 and 35 of the mandrel 28 are dimensioned such that the thickness of the annulus 33 is less than the thickness of the annulus 42. As a result, when the balloon 50 is formed, the distal end 51 thereof will have a thickness which is less than the remainder of the balloon.

Considering the process step described, it will be appreciated that a significant characteristic of this process step resides in the fact that when the balloon 50 is molded, it is simultaneously bonded to the catheter shaft. Thus, it may be said that the balloon is insert molded to the shaft, i.e., the shaft is inserted into a mold and the balloon is formed within the mold and simultaneously molded to the shaft.

As may be evident from considering the construction shown in FIG. 2, a number of advantages are realized when the process step of insert molding is employed to form a balloon and secure the balloon to a catheter shaft. For example, as compared to the process of molding a balloon and then securing the balloon to a catheter shaft, the process of insert molding is superior in one respect since the molding of the balloon and the securement of the balloon to the shaft occurs simultaneously. Additionally, from the point of view of the resulting product, a smooth transition between the balloon and the shaft will be intrinsically provided.

Another step of my process relates to providing a tip on the end of the catheter shaft 12. As previously indicated, in typical prior art processes the tip of the catheter was separately formed and subsequently glued to the distal end of the catheter shaft. In accordance with one embodiment of my process, the tip is insert molded onto the distal end of the catheter shaft. Apparatus which may be used to practice this part of my process are shown in FIGS. 6 and 7.

Figures 6, 7:
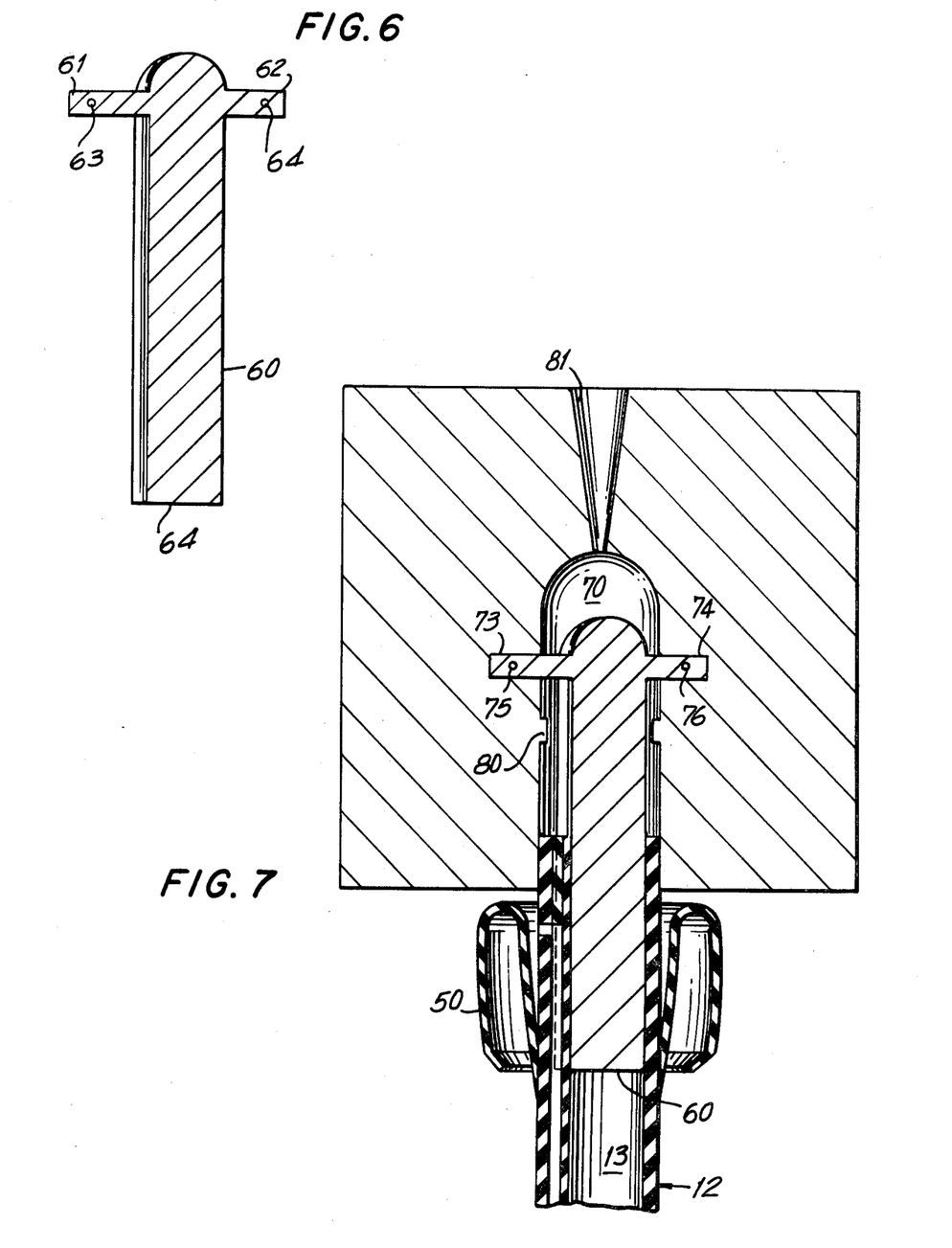
FIG. 6 is a view, in section, of a mold piece used in the practice of my process.
FIG. 7 is a view, in section of another mold used in the practice of my process.

Referring to FIG. 6, there is shown a guide 60 having two transversely extending members 61 and 62. At each end of the transversely extending members 61, 62, there is provided a hole 63, 64, respectively. As the first step in the formation of an insert molded tip, the end 64 of the guide 60 is inserted into the drainage lumen at the distal end of a catheter shaft, e.g. a catheter shaft of the type shown in FIG. 2. Referring to FIG. 7, the combination of the guide 60 and the catheter shaft 12 is then placed within the cavity 70 of a mold 71. The major portion of the cavity 70 is cylindrical and has an internal diameter equal to the external diameter of the catheter shaft 12. The mold 71 is similar to the mold 25 as shown in FIG. 5 in that the mold 71 is a two part mold which may be opened to expose the cavity 70. The cavity 70 includes transverse cut-outs 73, 74 which engagingly receive the transverse extensions 63, 64 of the guide 60. Additionally, pins 75, 76 may be inserted through the holes 63, 64 of the guide 60 and received in the cavity 70 so as to insure alignment of the guide 60. Similarly, the guide 60 may be provided with a transverse marking at some point longitudinally thereof which would indicate the depth to which the guide 60 should be inserted into the drainage lumen 13 of the catheter shaft 12. With further reference to the cavity 70 and the mold 71, it may be noted that the mold 71 protrudes annularly into the cavity 70 as indicated at 80.

Figure 3:
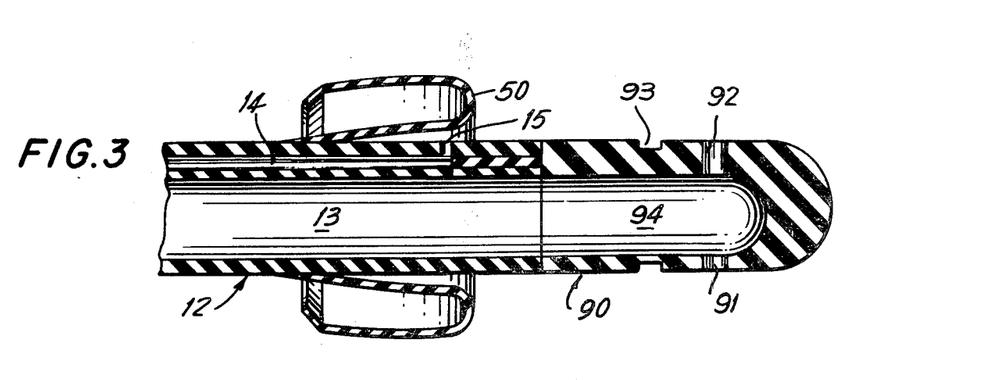

In FIG. 7 it may be noted that when the combination of the catheter shaft 12 and the guide 60 are disposed within the cavity 70 of the mold 71, the balloon 50 is rolled back. With this disposition of the components, the mold 71 is closed and an uncured elastomeric material is supplied, under pressure, through the supply channel 81. Preferably, the material thus supplied is a catalyzed, heat curable silicone rubber. In the event that such a heat curable material is used, the mold 71 is heated, by an appropriate means, until the supplied material is at least partially cured. When at least a partial curing thereof has been achieved, the mold 71 is opened and the catheter shaft 12 is removed. When removed, the catheter shaft 12 will include a hollow tip which is molded directly to the shaft 12. Of course, occupying the cavity within the hollow tip and extending into the shaft 12 will be the guide 60. However, protruding transversely through the walls of the tip will be the transverse extensions 63, 64 of the guide 60. Thus, the guide 60 may be conveniently removed by stretching the tip 70 and pushing the guide member 60 out through one of the two apertures or eyes which were defined by the transverse extensions 63, 64. When the guide 60 has been removed, a product will result of the type which is shown in FIG. 3. Referring to FIG. 3, it will be seen that a hollow tip 90 has been provided and is molded to the distal end of the shaft 12. The cavity 94 within the tip 90 is aligned with and forms an extension of the drainage lumen 13. Of course, the alignment of the cavity 90 with the drainage lumen 13 intrinsically occurs because of the presence of the guide 60 during the insert molding of the tip 90 onto the shaft 12. Similarly, the presence of the transverse extensions 61, 62 of the guide member 60 automatically provide the drainage eyes 91, 92 which provide fluid communication between the exterior of the tip 90 and the cavity 94 therein. Finally, it may be noted that the tip 90 is preferably provided with a peripheral groove 93 which arises because of the presence of the peripheral protuberance 80 within the cavity 70 of the mold 71.

Figure 4:
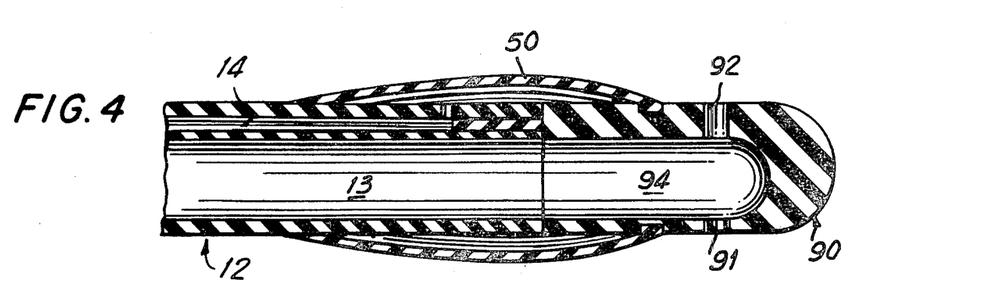

Once having obtained the construction shown in FIG. 3, the final step associated with the formation of the catheter tip assembly involves the bonding of the distal end of the balloon 50 to the tube 90. Thus, the balloon 50 is unrolled and, according to this preferred embodiment of my invention, the distal end of the balloon is received in the groove 93 and is therein bonded to the tube 90 so as to provide the final catheter construction as shown in FIG. 4. In connection with the fact that the distal end of the balloon is preferably received within the groove 93, it may be recalled that when the balloon was insert molded onto the catheter shaft, a preference was expressed for so conducting the molding operation as to insure that the internal diameter of the distal end of the balloon was less than the external diameter of the catheter shaft and, additionally, the thickness of the balloon at its distal end was less than the thickness of the remainder of the balloon. The preference for these dimensional requirements will be apparent from considering the catheter construction shown in FIGS. 3 and 4. Thus, it will be appreciated that if the internal diameter of the distal end of the balloon is less than the outer diameter of the catheter shaft, the distal end of the balloon will seat within the groove 93. Further, if the thickness of the balloon at its distal end is less than the thickness of the remainder of the balloon, the depth of the groove 93 may be minimized thus minimally impairing the strength of the tip while nevertheless insuring that a smooth transition is provided between the distal end of the tip and the distal end of the balloon.

In summary, it will be appreciated that two of the significant steps of my novel process are the insert molding of the balloon onto the catheter shaft and the insert molding of the tip onto the catheter shaft. By employing either one or both of these steps, manufacturing efficiencies are realized, a desirable product is produced and the catheter designer is provided with an added degree of freedom. For example, with respect to the last mentioned benefit, the process of my invention enables a catheter designer to select a material for the catheter tip without being inhibited as to the material requirements associated with the balloon. Thus, a material for the balloon may be selected which will insure that only a minimum inflation pressure is required in order to inflate the balloon, e.g. a material having a relatively low modulus of elasticity. On the other hand, through the use of my process, a material may be selected for the tip which is more rigid, e.g. has a higher modulus of elasticity than the material selected for the balloon.

Still another advantage of the construction resulting from the use of my process resides in the fact that one is no longer faced with the problem of bonding a separately formed tip to a separate catheter shaft and simultaneously endeavoring to maintain alignment between the two. In accordance with my process, a strong bond is inherently and automatically formed between the tip and the catheter shaft when the catheter tip is formed and alignment between the cavity of the hollow tip and the drainage lumen of the shaft is automatic.

Still another advantage of practicing the preferred form of my process relates to the fact that a catheter construction is produced which has a relatively smooth exterior surface, i.e. the transitions between the tip and the balloon or the balloon and the shaft are inherently smooth.

In addition to the above advantages, the catheters of the present invention are substantially stronger than prior art catheters in which a silicone rubber balloon and tip are attached to a silicone rubber catheter shaft by thermal bonding, solvent bonding (with a fugitive solvent), frictional and mechanical interlock or other known methods which do not require an adhesive or non-fugitive bonding agent. For example, catheters are obtained according to the present invention in which the pull strength between a silicone rubber tip and silicone rubber shaft is at least about 5 pounds and preferably at least 10 pounds. Depending somewhat on the French size of the specific catheter, the above pull strengths correspond to bond strengths of at least about 150 lbs/in$^2$, and preferably at least about 300 lbs/in$^2$.

The pull strengths noted above are determined by placing a catheter in a Scott tensile strength testing machine. In the machine, the catheter shaft is held by a first grip and the catheter tip is held by a second grip. The first and second grips are then pulled at a 180° angle with respect to each other at a rate of 12 inches/minute until the cather tip and shaft are pulled apart. The pull strength of the catheter being tested is the pounds pull on the catheter just prior to breakage. The bond strengths noted above are determined by dividing the pull strength by the area of the joint between the catheter tip and shaft.

Figure 8:
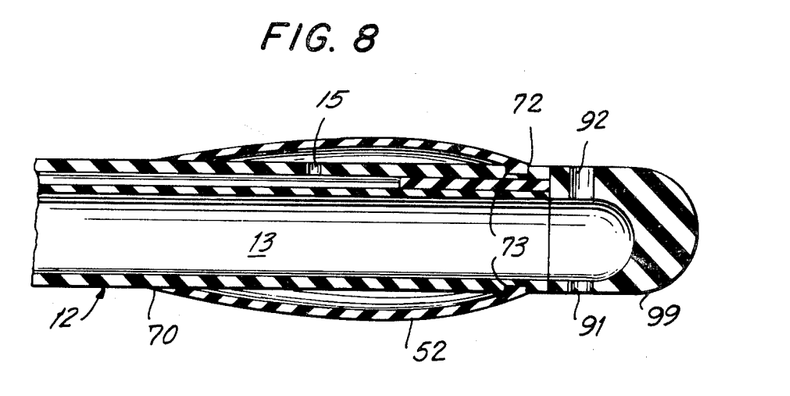
FIG. 8 is a fragmentary view, in section, of another embodiment of my invention.

It should be appreciated that although a preferred embodiment of my process has hereinbefore been recited, a number of modifications thereof may be employed if desired. For example, referring to the step of insert molding the balloon onto the catheter shaft, it will be recalled that the length of the resulting balloon section was such that the distal end of the balloon extended past the distal end of the catheter shaft. Obviously, such a resulting construction contemplates that the distal end of the balloon will be bonded to the tip of the catheter shaft. However, an acceptable catheter construction may be obtained by bonding the distal end of the balloon onto the catheter shaft rather than the tip. In order to achieve this construction, the annulus 40 shown in FIG. 5 would be longitudinally extended so that a longer longitudinal section of the shaft 12 was shielded. Similarly, the longitudinal length of the annulus 42 and the annulus 33 would be dimensioned appropriately. Thus, there would be produced a catheter of the type shown in FIG. 8 wherein the balloon 52 is molded to the shaft 12 on the proximal side of the aperture 15, as at 70, and is molded to the shaft 12 on the distal side of the aperture, as at 72. As may be noted, the top 99 shown in FIG. 8 is preferably shorter than the tip of the embodiment shown in FIG. 4. Additionally, the distal end of shaft 12, in FIG. 8, is preferably provided with a groove 73 which receives the distal end of the balloon 52. The groove 73 may be ground into the shaft.

Figure 9:
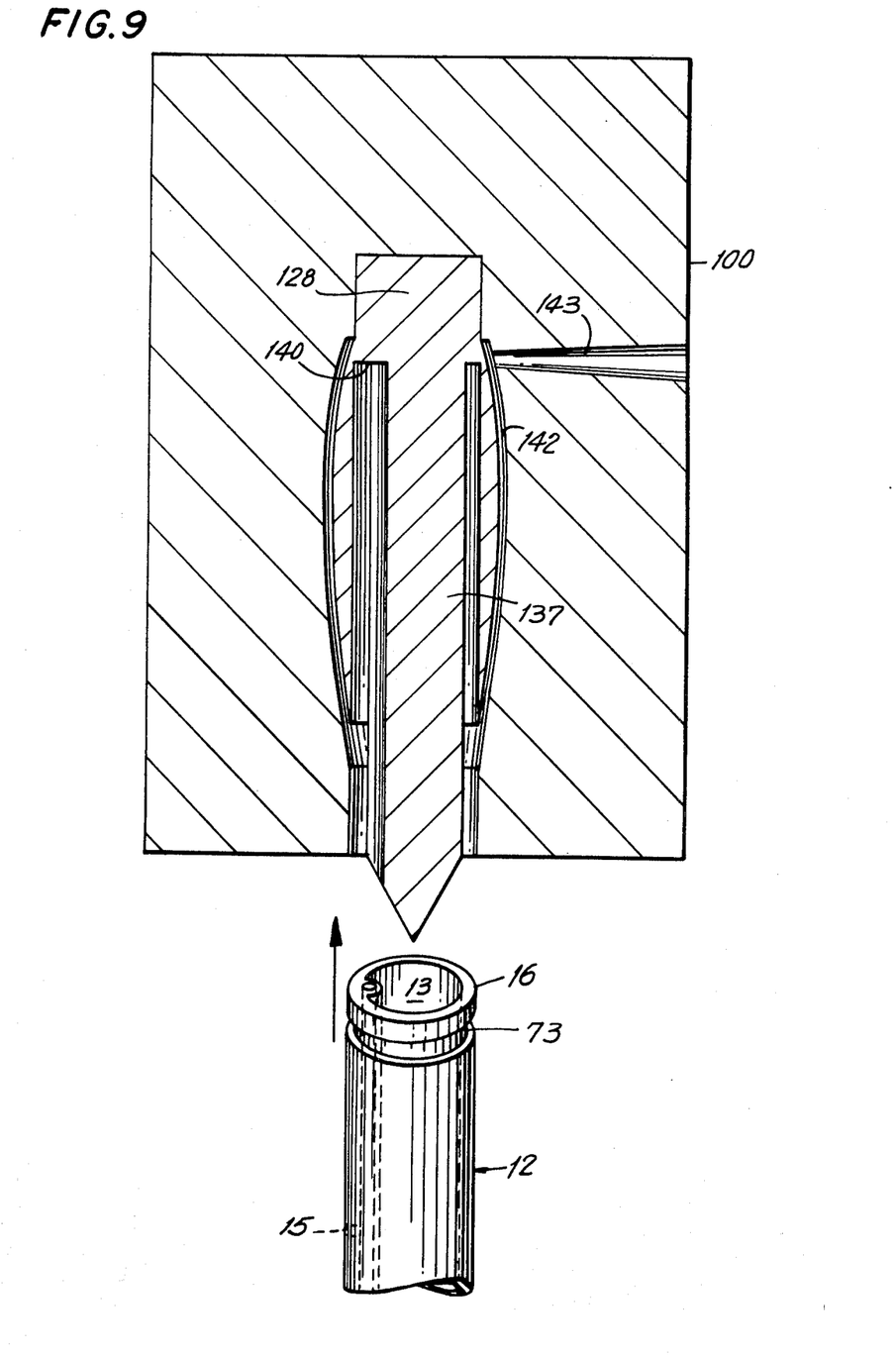
FIG. 9 is a view, in section, of a mold used to practice another embodiment of invention.

Referring to FIG. 9, a mold 100 is shown which may be used to insert mold a balloon which does not extend beyond the distal end of the shaft, i.e., a balloon shaft configuration of the type shown in FIG. 8 may be molded. Thus, referring to FIG. 9, the mold 100 would longitudinally separate to expose a cavity 126 which engagingly receives the mandrel 128. The wall of the mandrel 128 and the interior walls of the mold 100 define an annulus 142. A catheter shaft 12, preferably provided with a groove 73, is disposed over the exterior 137 such that the distal end 16 abuts the land 140. An uncured elastomeric material, preferably catalyzed, heat curable silicone rubber, is injected through the feed channel 143 to the annulus 142. If the injected elastomeric material is heat curable, the mold is then heated to at least partially cure the injected material. Thereafter, the mold 100 is split apart, the catheter shaft and molded balloon are removed and the mandrel 128 is withdrawn from the shaft. Subsequently, a tip may be molded onto the distal end of the catheter shaft as heretofore described with reference to FIG. 7 and thereafter the distal end of the balloon is bonded to the catheter shaft to produce a catheter of the type shown in FIG. 8.

Of course, it will be appreciated that with this approach, the inner diameter of the distal end of the resulting balloon cannot be made less than the outer diameter of the catheter shaft since a portion of the mandrel 128 must, at all times, shield the distal end of the catheter shaft. Since the inner diameter of the distal end of the balloon cannot be insert molded so as to be less than the outer diameter of the catheter shaft, it follows that some difficulty might be encountered in trying to avoid wrinkles in the balloon when the distal end thereof is attached to the catheter shaft.

However, if it is desired to make a catheter wherein the balloon is not attached to the tip while nevertheless avoiding the problem of possibly encountering wrinkles at the bonding site, another embodiment of my process may be employed wherein the balloon is insert molded to the catheter shaft on the distal side of the aperture 15 and then bonded to the shaft on the proximal side of the aperture 15. For example, FIG. 10 discloses a longitudinally separable mold 200. A mandrel 238 is engagingly received within a cavity within the mold 200, thus defining an annulus 242. When the mold 200 and the mandrel 238 are assembled, a catheter 12 is inserted into the mold 200 and over the depending portion 237 of the mandrel 238. The depending portion 237 may be provided with a groove 236 which receives the radial protuberance associated with the inflation lumen. When inserted, the exterior wall of the catheter shaft abuts the interior wall of the mold 200 in the region 220 and 221. Preferably, the catheter shaft 12 is provided with a groove 75 on the proximal side of the aperture 15. The shaft 12 is inserted until the distal end 16 abuts the land 240.

Figure 10:
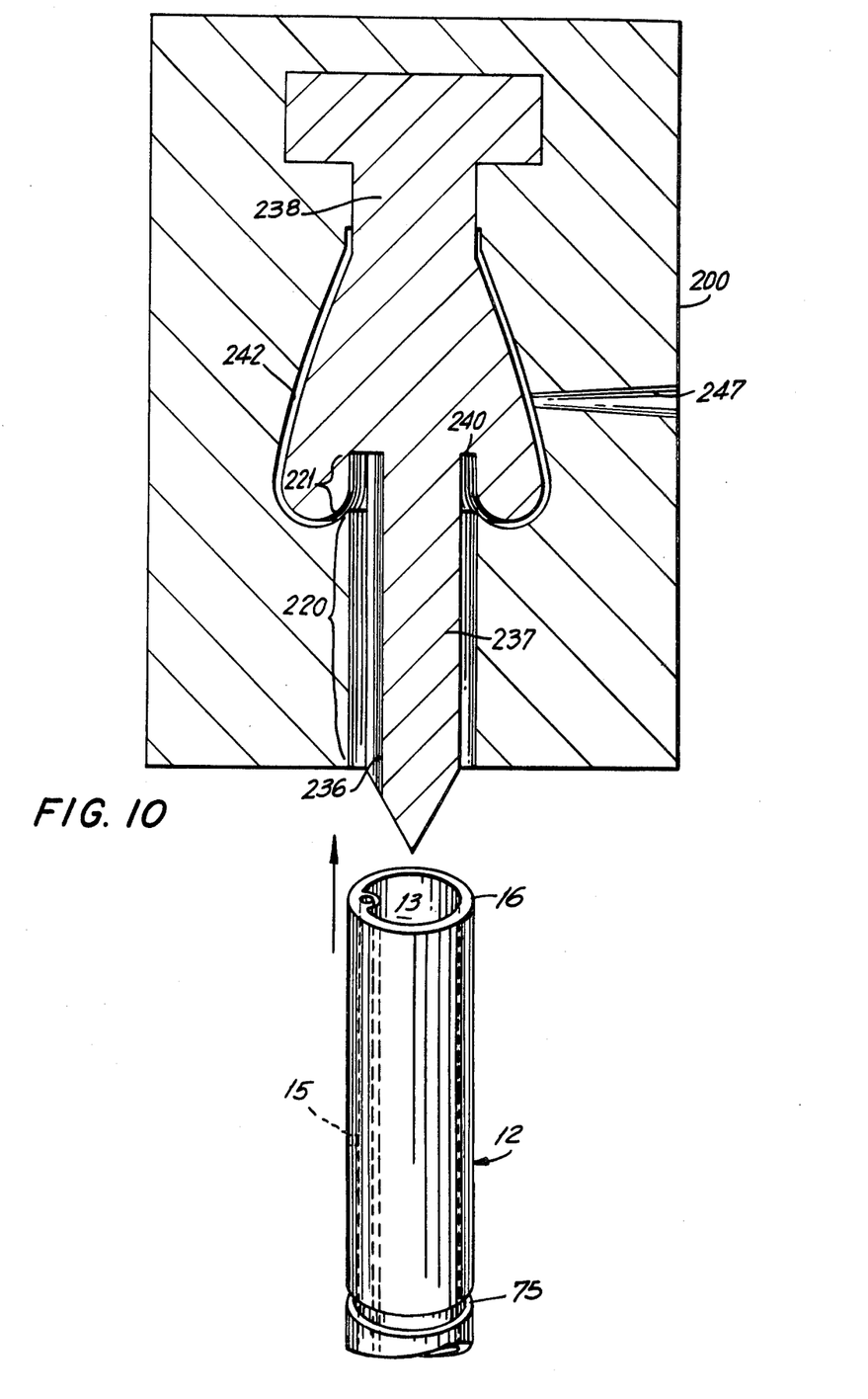
FIG. 10 is a view, in section, of a mold used to practice another embodiment of invention.
Figure 11:
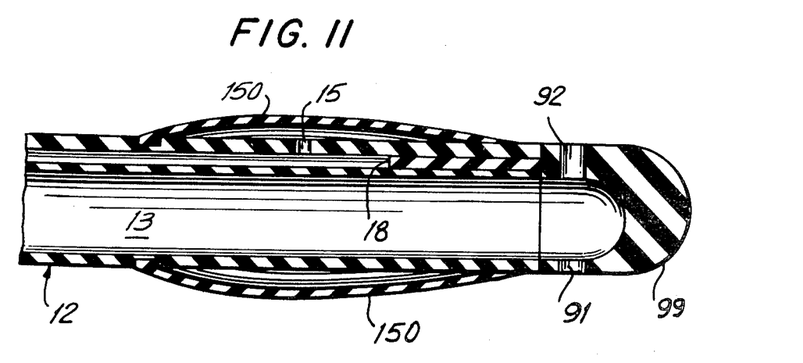
FIG. 11 is a fragmentary view, in section, of an embodiment of my invention.

When the mold, mandrel and catheter shaft have been thus assembled, an elastomeric, uncured material is injected through the feed channel 247 and fills the annulus 242. Preferably, the injected material is a catalyzed, heat curable silicone rubber, in which event the mold is heated after injection to at least partially cure the material in the annulus. Thereafter, the mold is separated and the shaft, balloon and mandrel are removed. The balloon is then unrolled onto the shaft and the shaft is removed from the mandrel. Subsequently, a tip may be insert molded onto the distal end 16 of the shaft 12 through a process of the type shown in FIG. 7 and the proximal end of the balloon is bonded to the tip, e.g., within the groove 75. Thus, there is produced a catheter construction of the type shown in FIG. 11 wherein the distal end of the balloon 150 is molded to the shaft 12 on the distal side of the aperture 15 and is bonded to the catheter, i.e. to the shaft 12, on the proximal side of the aperture 15 and a tip 99, having drainage eyes 91, 92 is molded to the distal end of the shaft 12.

Referring again to FIG. 10, a close inspection thereof will reveal that through the use of this embodiment of my invention, the balloon may be insert molded to the catheter shaft, on the distal side of the aperture 15 and the proximal end of the balloon may be formed with a diameter which is less than the outer diameter of the catheter shaft. Thus, when the balloon is rolled back onto the catheter shaft, the proximal end of the balloon may be received in the groove 75 without wrinkling.

While the embodiments described above all relate to a retention catheter in which both a tip and balloon are insert molded onto a catheter shaft, it should be understood that it is within the scope of the present invention to insert mold the tip but not the balloon onto the catheter shaft or, alternatively, to insert mold the balloon but not the tip onto the catheter shaft. In these embodiments of the invention, the component of the catheter which is not insert molded to the shaft is attached to the catheter shaft by conventional technique. Indeed, in the commercially preferred embodiment of the present invention, the tip is first insert molded onto the catheter shaft and thereafter the proximal end of a preformed balloon sleeve is bonded by an adhesive to the catheter shaft, and the distal end of the balloon sleeve is bonded by an adhesive to the catheter tip.

It should also be understood that the present invention is not limited to retention catheters and the method of making such catheters. That is, non-retention catheters, which do not require an inflatable balloon, and the method of making such catheters are within the scope of the present invention. In this embodiment of the invention, a suitable guide, e.g. the guide shown in FIG. 6, is inserted into a catheter shaft similar to the one shown in FIG. 1, but without inflation lumen 14 and aperture 15. Thereafter, the shaft with the slide therein is inserted into a suitable mold and the tip is insert molded onto the shaft as generally described above with respect to the discussion of FIG. 7. Of course, since a non-retention catheter does not require a balloon, the mold used in this embodiment of the invention is not notched so as to provide a groove for receiving a balloon such as shown in FIG. 3.

With general regard to all of the embodiments of my method heretofore described, it is preferable to employ an extruded catheter shaft which is only partially cured. Additionally, when the balloon and/or the tip are molded onto the shaft, it is preferable to only partially cure the balloon and the shaft. It is preferable to only partially cure the balloon and tip and to use a partially cured shaft in order that the resulting product may be cured (post-cured) as a unit. Such a post-curing had been found to provide a stronger unitary product.

With respect to materials, it is preferred to use silicone rubber for the shaft, tip and the balloon. Additionally, the preferable agent for bonding the balloon to the shaft is a catalyzed uncured, heat curable silicone rubber.

Finally, with respect to the embodiments relating to urinary retention catheters, those skilled in the art will appreciate urinary retention catheters are generally provided with two funnels at the proximal end of the shaft, one funnel associated with the drainage lumen and one associated with the inflation lumen. Such funnels, and the method by which they are attached to the catheter shaft, are well known, e.g., Birtwell discloses such a pair of funnels.

Although a number of embodiments of my invention have hereinabove been described, it will be apparent that still other variations may be perceived by those skilled in this art while nevertheless not departing from the scope of my invention as defined in the claims appended hereto.

I claim:

1. The process of manufacturing a catheter which comprises:
   a. providing an elastomeric catheter shaft having a drainage lumen extending longitudinally thereof;
   b. inserting a guide in the drainage lumen of said shaft;
   c. inserting at least a portion of said shaft, including at least a portion of said guide in a mold;
   d. molding a hollow tip and simultaneously bonding said tip to the distal end of said shaft by introducing elastomeric material under pressure into said mold; and
   e. providing at least one drainage eye through said tip and communicating via the hollow tip with said drainage lumen.

2. The process of claim 1 wherein said at least one drainage eye is formed when said hollow tip is molded and simultaneously bonded to said shaft.

3. The process of claim 1 wherein said shaft and said tip are silicone rubber.

4. The process of claim 3 wherein said shaft is an extruded shaft.

5. The process of claim 1 further comprising removing the guide from the interior of the catheter by passing said guide through said at least one drainage eye.

6. The process of claim 1 wherein the pull strength between said tip and said shaft is at least about 5 pounds.

7. The process of claim 6 wherein the bond strength between said tip and shaft is at least about 150 lbs./in.$^2$.

8. The process of claim 1 wherein said guide is inserted into the drainage lumen so that it extends distally in said mold at least substantially to the distal end of said shaft.

9. The process of manufacturing a catheter which comprises:
   a. providing an elastomeric catheter shaft having a drainage lumen extending longitudinally thereof and an inflation lumen extending longitudinally for at least a major portion thereof and communicating with the exterior of said shaft through an aperture adjacent the distal end of said shaft;
   b. inserting a guide in the drainage lumen of said shaft;
   c. inserting at least a portion of said shaft, including at least a portion of said guide in a mold;
   d. molding a hollow tip and simultaneously bonding said tip to the distal end of said shaft with said guide inserted therein by introducing elastomeric material under pressure into said mold;
   e. bonding one end of a balloon sleeve to the catheter shaft on the proximal side of said aperture and the other end of the balloon sleeve to the catheter on the distal side of said aperture; and
   f. providing at least one drainage eye through said tip and communicating via the hollow tip with said drainage lumen.

10. The process of claim 9 which further includes the step of providing a peripheral groove in the exterior of the shaft on the distal side of said aperture and bonding said balloon sleeve to said shaft within said groove.

11. The process of claim 9 further comprising removing the guide from the interior of the catheter by passing said guide through said at least one drainage eye.

12. The process of claim 9 wherein said at least one drainage eye is formed when said hollow tip is molded and simultaneously bonded to said shaft.

13. The process of claim 9 wherein said guide is inserted into the drainage lumen so that it extends distally in said mold at least substantially to the distal end of said shaft.

14. The process of claim 9 wherein said other end of the balloon sleeve is bonded to said tip.

15. The process of claim 14 which further includes the step of molding a peripheral groove into the exterior of said tip when said tip is molded and simultaneously bonded to said shaft.

16. The process of claim 9 wherein said shaft, said balloon sleeve and said tip are silicone rubber.

17. The process of claim 16 wherein said shaft is an extruded shaft.

18. The process of manufacturing a catheter which comprises:
   a. providing an elastomeric catheter shaft having a drainage lumen extending longitudinally thereof and an inflation lumen extending for at least a major portion thereof and communicating with the exterior of said shaft through an aperture adjacent the distal end of said shaft;
   b. inserting at least a portion of said shaft into a mold and inserting a mandrel into the drainage lumen of said shaft;
   c. molding a balloon sleeve and simultaneously bonding said balloon sleeve to said shaft adjacent the distal end thereof and on one side of said aperture by introducing elastomeric material under pressure to said mold;
   d. bonding a hollow tip to the distal end of said shaft;
   e. providing at least one drainage eye through said tip and communicating via the hollow tip with said drainage lumen; and
   f. bonding the exposed end of said balloon sleeve to said catheter on the other side of said aperture.

19. The process of claim 18 wherein said shaft, said balloon sleeve and said tip are silicone rubber.

* * * * *